United States Patent [19]

Robbins

[11] Patent Number: 5,554,762
[45] Date of Patent: Sep. 10, 1996

[54] PROCESS FOR THE PREPARATION OF 1,1'-METHANE-BIS (HYDANTOIN)

[75] Inventor: Jeffrey D. Robbins, Berkeley, Calif.

[73] Assignee: Zeneca Limited, London, England

[21] Appl. No.: 442,231

[22] Filed: May 15, 1995

[51] Int. Cl.$^6$ .................. C07D 233/40; C07D 233/72
[52] U.S. Cl. ............................................. 548/314.1
[58] Field of Search ............................ 548/314.1

[56] References Cited

U.S. PATENT DOCUMENTS

| | | | |
|---|---|---|---|
| 2,418,000 | 3/1947 | Walker | 548/314.1 |
| 2,876,062 | 3/1959 | Torke et al. | 548/314.1 X |
| 3,225,060 | 12/1965 | Johnson | 548/314.1 |
| 4,578,224 | 3/1986 | Bayer et al. | 548/314.1 |
| 5,399,759 | 3/1995 | Rodriguez | 564/214 |

FOREIGN PATENT DOCUMENTS

| | | | |
|---|---|---|---|
| 0450543 | 8/1968 | Canada | 548/314.1 |
| 0450550 | 8/1968 | Canada | 548/314.1 |

OTHER PUBLICATIONS

R. Behrend and R. Niemeyer, "Condensatin von Hydantoin mit Formaldehyd", *Annalen*, 1909, vol. 365, pp. 38–49.

*Primary Examiner*—Floyd D. Higel
*Attorney, Agent, or Firm*—Joseph R. Snyder

[57] ABSTRACT

This invention relates to method for the preparation of 1,1'-methane-bis(hydantoin). 1,1'-methane-bis(hydantoin) is an intermediate in the preparation of N-(phosphonomethyl)glycine which is a well known herbicide and plant growth regulator.

7 Claims, No Drawings

PROCESS FOR THE PREPARATION OF 1,1'-METHANE-BIS (HYDANTOIN)

This invention relates to an improved method for the preparation of 1,1'-methanebis(hydantoin), hereinafter MBH, a compound having the following formula:

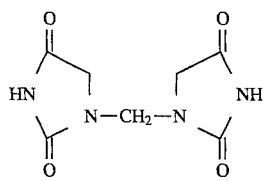

MBH is an intermediate in a method of the preparation of N-(phosphonomethyl)glycine (PMG), which is disclosed in U.S. Pat. No. 4,578,224. The compound N-(phosphonomethyl)glycine is a well known herbicide and plant growth regulator.

BACKGROUND OF THE INVENTION

U.S. Pat. No. 2,418,000 discloses the preparation of MBH from hydantoin and a formaldehyde source including paraformaldehyde, anhydrous formaldehyde gas or 37% formaldehyde solution in the presence of HCl and water, wherein the concentration of water is between 13–30 weight percent of the reaction mixture. The preferred concentration of water is between 18–27 weight percent. The specification of U.S. Pat. No. 2,418,000 specifically states that if the water content of the reaction mixture is greater than 30 weight percent, the desired product is produced in very low yields. Although the preferred embodiment of that procedure is reported to give MBH in 87% yield, the amount of solvent used is so small, and MBH is so insoluble that the reaction mixture solidifies upon completion of the reaction. A solidified product in the reaction vessel is undesirable because of the increased handling procedures required to remove and/or transfer the product.

Due to the importance of N-(phosphonomethyl)glycine, new and alternative methods of preparation of this beneficial herbicide are continually being explored. In addition, newly improved methods of preparation are also desirable.

It is an object of the present invention to provide an improved method for the preparation of MBH. It is a further object of this invention to reduce the cost of producing PMG by increasing the reaction yield of MBH. A still further object of this invention is to include in the reaction medium a sufficient amount of water to produce a stirrable reaction mixture, thereby increasing ease of product handling

SUMMARY OF THE INVENTION

It has now been surprisingly found that an increase in the initial weight percent of water in the reaction mixture of hydantoin and the formaldehyde source to generate MBH is beneficial to the percent yield of the product. It has now been found that the reaction can be carried out in 95–97% yield with an initial water content of the reaction mixture equal to 35–90% weight percent and stoichiometric amounts of reactants. This water content represents at least a two-fold increase of what was previously regarded as the preferred amount.

This invention may be summarized as a method for the synthesis of 1,1'-methanebis(hydantoin) comprising: contacting hydantoin with a formaldehyde source in an aqueous medium containing about 35–90% water and a strong protic acid.

DETAILED DESCRIPTION OF THE INVENTION

The starting compounds for this process are; hydantoin, a formaldehyde source, a protic acid and water. The reaction may be schematically represented as follows:

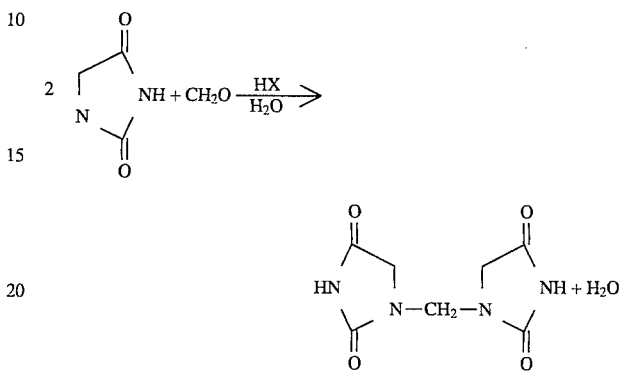

wherein $CH_2O$ represents a formaldehyde source described in detail below and HX is a protic acid.

Hydantoin is present in the reaction mixture in approximately stoichiometric amount compared to the formaldehyde source. Thus, the preferred amount is a 2:1 molar ratio of hydantoin to the formaldehyde source.

As shown in the examples below, paraformaldehyde or about a 37% formaldehyde solution may be used interchangeably as the formaldehyde source. In addition, the formaldehyde source may be anhydrous formaldehyde gas or a formaldehyde alcohol complex. The formaldehyde alcohol complex is described in detail in U.S. Pat. No. 5,399,759.

The formaldehyde alcohol complex is a means for providing a formaldehyde reactant to a chemical process by contacting paraformaldehyde with about 0.25 to about 3 mole equivalent of an aliphatic alcohol, in the presence of a catalytic amount of a base, and then providing the product to the process.

The preferred formaldehyde source is paraformaldehyde or about a 37% formaldehyde solution.

The preferred acid used in this process is concentrated hydrochloric acid; however, other strong protic acids are suitable. Other suitable acids include hydrobromic, hydroiodic, sulfuric, and phosphoric acids. These acids may be regarded as strong protic acids. The concentration of the protic acid should be about 3–6 mole equivalents of acid per mole equivalent of formaldehyde source.

The reaction may proceed by first adding hydantoin, followed by the formaldehyde source, and while stirring, adding concentrated hydrochloric acid. However, the exact sequence of reactant addition is not important. The total water content of the initial reaction mixture is about 35–90 weight %, the preferred amount is about 35–75 weight % and the most preferred amount is about 35–50 weight %. At the end of the reaction period water is added, the reaction mixture is filtered and the MBH product is dried.

The following examples serve to illustrate this invention:

EXAMPLE 1

To a nitrogen purged three-neck round bottom flask equipped with overhead stirrer, water condenser and nitrogen line were added 10.11 grams (100 mmol) of 99% hydantoin and 1.58 grams (50 mmol) of 95% paraformaldehyde. While the mixture was stirred, 14 mL of concentrated HCl was added. The mixture was stirred at room temperature overnight. The initial water content in this reaction mixture was 37 % by weight.

After about 20 hours, 15 mL of water was added to the mixture, and the reaction mixture was filtered through a fritted glass funnel. The resulting white cake was washed with water and dried overnight in a vacuum oven to afford 10.26 g of 1,1'-methane-bis(hydantoin) as a snow white powder. The identity of the product was confirmed by mass spectrometry, $^1$H NMR and $^{13}$C NMR. The purity of the product was determined to be 99% by quantitative $^1$H NMR spectroscopy using 99.7% 1,4-dichlorobenzene as an internal standard. Hence, the corrected yield of MBH was 95%.

EXAMPLE 2

To a nitrogen purged three-neck round bottom flask equipped with overhead stirrer, water condenser and nitrogen line were added 10.11 grams (100 mmol) of 99% hydantoin and 1.58 grams (50 mmol) of 95% paraformaldehyde. While the mixture was stirred, 21 mL of concentrated HCl was added. The mixture was stirred at room temperature overnight. The initial water content in this reaction mixture was 42 % by weight.

After about 26 hours, 21 mL of water was added to the mixture and the reaction mixture was filtered through a fritted glass funnel. The resulting white cake was washed with water and dried overnight in a vacuum oven to afford 10.24 g of 1,1'-methane-bis(hydantoin) as a snow white powder. The identity of the product was confirmed by mass spectrometry, $^1$H MR and $^{13}$C NMR. The purity of the product was determined to be 100% by quantitative $^1$H MR spectroscopy using 99.7% 1,4-dichlorobenzene as an internal standard. Hence, the corrected yield of MBH was 97%.

EXAMPLE 3

To a nitrogen purged three-neck round bottom flask equipped with overhead stirrer, water condenser and nitrogen line were added 10.11 grams (100 mmol) of 99% hydantoin and 3.8 mL (4.1 g) of 36% formaldehyde in water (50 mool). A pipette was used to add the formaldehyde solution to the reaction flask. While the mixture was stirred, 14 mL of concentrated HCl was added. The mixture was stirred at room temperature overnight. The initial water content in this reaction mixture was 42% by weight.

After about 18 hours, 14 mL of water was then added to the mixture and the reaction mixture was filtered through a flitted glass funnel. The resulting white cake was washed with water and dried overnight in a vacuum oven to afford 10.43 g of 1,1'-methanebis(hydantoin) as a snow white powder. The identity of the product was confirmed by mass spectrometry, $^1$H NMR and $^{13}$C NMR. The purity of the product was determined to be 99% by quantitative $^1$H NMR spectroscopy using 99.7% 1,4-diichlorobenzene as an internal standard. Hence, the corrected yield of MBH was 97%.

EXAMPLE 4

To a nitrogen purged three-neck round bottom flask equipped with overhead stirrer, water condenser and nitrogen line were added 10.11 grams (100 mmol) of 99% hydantoin and 3.8 mL (4.1 g) of 36% formaldehyde in water (50 retool). A pipette was used to add the formaldehyde solution to the reaction flask. While the mixture stirred 21 mL of concentrated HCl was added. The mixture was stirred at room temperature overnight. The initial water content in this reaction mixture was 47% by weight.

After about 18 hours passed, 21 mL of water was then added to the mixture and the reaction mixture was filtered through a flitted glass funnel. The resulting white cake was washed with water and dried overnight in a vacuum oven to afford 10.26 g of 1,1'-methanebis(hydantoin) as a snow white powder. The identity of the product was confirmed by mass spectrometry, $^1$H NMR and $^{13}$C NMR. The purity of the product was determined to be 100% by quantitative $^1$H NMR spectroscopy using 99.7% 1,4-dichlorobenzene as an internal standard. Hence, the corrected yield of MBH was 97%.

What is claimed is:

1. A method for the synthesis of 1,1'-methane-bis(hydantoin) comprising: reacting hydantoin with a formaldehyde source selected from the group consisting of paraformaldehyde, a 37% formaldehyde solution, formaldehyde gas and a formaldehyde alcohol complex, wherein about two moles of hydantoin are used per mole of said formaldehyde source, in an aqueous medium containing about 35–90 % by weight initial water content and a strong protic acid, wherein the concentration of the strong protic acid is between 3 to 6 mole equivalent of acid per mole equivalent of formaldehyde source.

2. The method according to claim 1, wherein said strong protic acid is selected from the group consisting of hydrochloric acid, hydrobromic acid, hydroiodic acid, sulfuric acid, and phosphoric acid.

3. A method according to claim 1, wherein the initial water content is about 35–70%.

4. A method according to claim 1, wherein the initial water content is about 35–50%.

5. A method according to claim 1, wherein the formaldehyde source is paraformaldehyde.

6. A method according to claim 1, wherein the formaldehyde source is about a 37% formaldehyde solution.

7. In a process for producing 1,1'-methane-bis(hydantoin) of the type wherein hydantoin is reacted with formaldehyde in an aqueous reaction mixture containing about two moles of hydantoin per mole of formaldehyde and a strong protic acid, wherein the concentration of the strong protic acid is between 3 to 6 mole equivalent of acid per mole equivalent of formaldehyde, the improvement comprising: water in an initial amount of 35 to 90 % by weight.

\* \* \* \* \*